US00PP23294P2

(12) United States Plant Patent
van den Hoogen

(10) Patent No.: US PP23,294 P2
(45) Date of Patent: Jan. 1, 2013

(54) VERONICA PLANT NAMED 'ALLLORD'

(50) Latin Name: *Veronica longifolia*
Varietal Denomination: Alllord

(75) Inventor: Wilhelmus T. J. van den Hoogen, Cuijk (NL)

(73) Assignee: AllPlants Holding B.V., Cuijk (NL)

( * ) Notice: Subject to any disclaimer, the term of this patent is extended or adjusted under 35 U.S.C. 154(b) by 0 days.

(21) Appl. No.: 13/199,168

(22) Filed: Aug. 22, 2011

(51) Int. Cl.
*A01H 5/00* (2006.01)

(52) U.S. Cl. ..... Plt./251

(58) Field of Classification Search ..... Plt./251
See application file for complete search history.

*Primary Examiner* — Kent L Bell
(74) *Attorney, Agent, or Firm* — C. A. Whealy

(57) ABSTRACT

A new and distinct cultivar of *Veronica* plant named 'Alllord', characterized by its upright plant habit; freely flowering habit; compact and dense inflorescences with numerous intense dark violet-colored flowers; long flowering period; and potential to be used as a cut flower or as a container plant.

3 Drawing Sheets

Botanical designation: *Veronica longifolia.*
Cultivar denomination: 'ALLLORD'.

BACKGROUND OF THE INVENTION

The present invention relates to a new and distinct cultivar of *Veronica* plant, botanically known as *Veronica longifolia* and hereinafter referred to by the name 'Alllord'.

The new *Veronica* plant is a product of a planned breeding program conducted by the Inventor in Cuijk, The Netherlands. The objective of the breeding program is to create new attractive *Veronica* plants that can be used as either a cut flower or as a container plant.

The new *Veronica* plant originated from an open-pollination in September, 2008 of a proprietary selection of *Veronica longifolia* identified as code number 1-2008-30-3, not patented, as the female, or seed, parent with an unknown selection of *Veronica longifolia* as the male, or pollen, parent. The new *Veronica* plant was discovered and selected by the Inventor as a single flowering plant from within the progeny of the stated open-pollination in a controlled environment in Cuijk, The Netherlands in July, 2009.

Asexual reproduction of the new *Veronica* plant by vegetative cuttings in a controlled environment in Cuijk, The Netherlands, since September, 2009, has shown that the unique features of this new *Veronica* plant are stable and reproduced true to type in successive generations.

SUMMARY OF THE INVENTION

Plants of the new *Veronica* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Alllord'. These characteristics in combination distinguish 'Alllord' as a new and distinct *Veronica* plant:

1. Upright plant habit.
2. Freely flowering habit.

3. Compact and dense inflorescences with numerous intense dark violet-colored flowers.
4. Long flowering period.
5. Can be used as a cut flower or as a container plant.

Plants of the new *Veronica* differ primarily from plants of the female parent selection in the following characteristics:

1. Inflorescences of plants of the new *Veronica* are more compact than inflorescences of plants of the female parent selection.
2. Plants of the new *Veronica* and the female parent selection differ in flower color as plants of the female parent selection have dark pink-colored flowers.

Plants of the new *Veronica* can be compared to plants of *Veronica longifolia* 'Alllove', disclosed in U.S. Plant Pat. No. 21,478. In side-by-side comparisons conducted in Cuijk, The Netherlands, plants of the new *Veronica* differed primarily from plants of 'Alllove' in the following characteristics:

1. Plants of the new *Veronica* had narrower and darker green-colored leaves than plants of 'Alllove'.
2. Plants of the new *Veronica* and 'Alllove' differed in flower color as plants of 'Alllove' had red purple-colored flowers.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet comprises a side perspective view of a typical flowering plant of 'Alllord' grown in a 13-cm container.

The photograph on the second sheet is a close-up view of typical inflorescences of 'Alllord'.

The photograph on the third sheet is a close-up view of typical leaves of 'Alllord'.

DETAILED BOTANICAL DESCRIPTION

Plants used for the aforementioned photographs and following description were grown during the spring and early summer in an outdoor nursery in Cuijk, The Netherlands and under environmental conditions and cultural practices which closely approximate commercial production. During the production of the plants, day temperatures ranged from 12° C. to 28° C. and night temperatures ranged from 4° C. to averaged 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Veronica longifolia* 'Alllord'.

Parentage:

*Female, or seed, parent*.—Proprietary selection of *Veronica longifolia* identified as code number 1-2008-30-3, not patented.

*Male, or pollen, parent*.—Unknown selection of *Veronica longifolia*, not patented.

Propagation:

*Type cutting*.—Vegetative cuttings.

*Time to initiate roots*.—About 10 to 14 days at 12° C. to 30° C.

*Time to produce a rooted young plant*.—About 24 to 32 days at 12° C. to 30° C.

*Root description*.—Fine, fleshy; white in color.

*Rooting habit*.—Freely branching; dense.

Plant description:

*Plant type*.—Herbaceous perennial.

*Plant and growth habit*.—Upright inverted triangle; freely basal branching habit with about 24 main stems; moderately vigorous growth habit.

*Plant height*.—About 54.5 cm.

*Plant width*.—About 45.7 cm.

*Lateral branch description*.—Length: About 43.2 cm. Diameter: About 4 mm. Internode length: About 3.6 cm. Strength: Strong. Texture: Smooth, glabrous. Color: Close to 144A.

Foliage description:

*Arrangement*.—Opposite, simple.

*Length*.—About 8.3 cm.

*Width*.—About 2.5 cm.

*Shape*.—Lanceolate.

*Apex*.—Narrowly acute.

*Base*.—Truncate.

*Margin*.—Serrate.

*Texture, upper and lower surfaces*.—Smooth, glabrous.

*Venation pattern*.—Pinnate.

*Color*.—Developing leaves, upper surface: Between 138A and 143A. Developing leaves, lower surface: Between 143B and 144A. Fully expanded leaves, upper surface: Slightly darker than between N137A and 147A; venation, close to 144A to 144B. Fully expanded leaves, lower surface: Close to 147B; venation, close to 144B to 144C.

*Petiole length*.—About 1 cm.

*Petiole diameter*.—About 2.5 mm by 3 mm.

*Petiole texture, upper and lower surfaces*.—Smooth, glabrous.

*Petiole color, upper and lower surfaces*.—Close to 144C.

Flower description:

*Flower arrangement and shape*.—Single campanulate flowers arranged on primary and secondary terminal racemes; racemes compact and dense; flowers face mostly outwardly.

*Flowering habit*.—Freely flowering, each terminal branch has one primary raceme and about six secondary racemes; about 200 flowers per primary inflorescence and about 150 flowers per secondary inflorescence.

*Fragrance*.—None detected.

*Natural flowering season*.—Plants begin flowering about seven weeks after pinching; flowering continuous from June to late September in The Netherlands.

*Flower longevity on the plant*.—About one week; flowers not persistent.

*Flower buds*.—Length: About 4 mm. Diameter: About 2 mm. Shape: Broadly oblong. Color: Close to N88A; calyx, close to 143B.

*Inflorescence height*.—About 9.6 cm.

*Inflorescence diameter*.—About 2 cm.

*Flower diameter*.—About 6 mm.

*Flower height*.—About 8 mm.

*Petals*.—Quantity and arrangement: About five in a single whorl, petals fused about 50% of the length from the base. Length: About 6 mm. Width: About 3 mm. Shape: Obovate. Apex: Obtuse. Margin: Entire. Texture, upper surface: Mostly smooth and glabrous; towards the base, moderately pubescent. Texture, lower surface: Smooth, glabrous. Color: When opening, upper and lower surfaces: Close to N88A; towards the base, close to 157D. Fully opened, upper and lower surfaces: Close to N88A to N88B; towards the base, close to 157D.

*Sepals*.—Quantity and arrangement: About four in a single whorl, sepals fused about 5% of the length from the base. Length: About 2 mm to 2.5 mm. Width: About 1 mm. Shape: Ovate. Apex: Acute. Margin: Entire. Texture, upper and lower surfaces: Smooth, glabrous. Color: When opening, upper and lower surfaces: Close to 143B. Fully opened, upper and lower surfaces: Close to 143A.

*Peduncles*.—Length: About 12.6 cm. Diameter: About 3 mm. Aspect: Primary racemes, mostly upright; secondary racemes, about 35° from vertical. Strength: Strong. Texture: Smooth, glabrous. Color: Close to 144B.

*Pedicels*.—Length: About 1 mm. Diameter: About 0.5 mm. Aspect: About 60° from peduncle axis. Strength: Moderately strong. Texture: Smooth, glabrous. Color: Close to 144B tinged with close to N186B.

*Reproductive organs*.—Stamens: Quantity per flower: One or two. Filament length: About 4.5 mm. Filament color: Close to N88B. Anther length: About 1.5 mm. Anther shape: Narrowly reniform. Anther color: Between N88A and N92B. Pollen amount: Scarce. Pollen color: Close to 156D.

*Pistils*.—Quantity per flower: One. Pistil length: About 5 mm. Stigma shape: Clavate. Stigma color: Close to N89A. Style length: About 4.5 mm. Style color: Close to N88B to N88C. Ovary color: Close to 143B.

*Seeds and fruits*.—Seed and fruit development has not been observed on plants of the new *Veronica*.

Disease & pest resistance: Plants of the new *Veronica* have not been noted to be resistant to pathogens and pests common to *Veronica*.

Garden performance: Plants of the new *Veronica* have exhibited good garden performance and to be tolerant to rain, wind, high temperatures of about 35° C. and to be hardy to USDA Hardiness Zone 4.

It is claimed:

1. A new and distinct *Veronica* plant named 'Alllord' as illustrated and described.

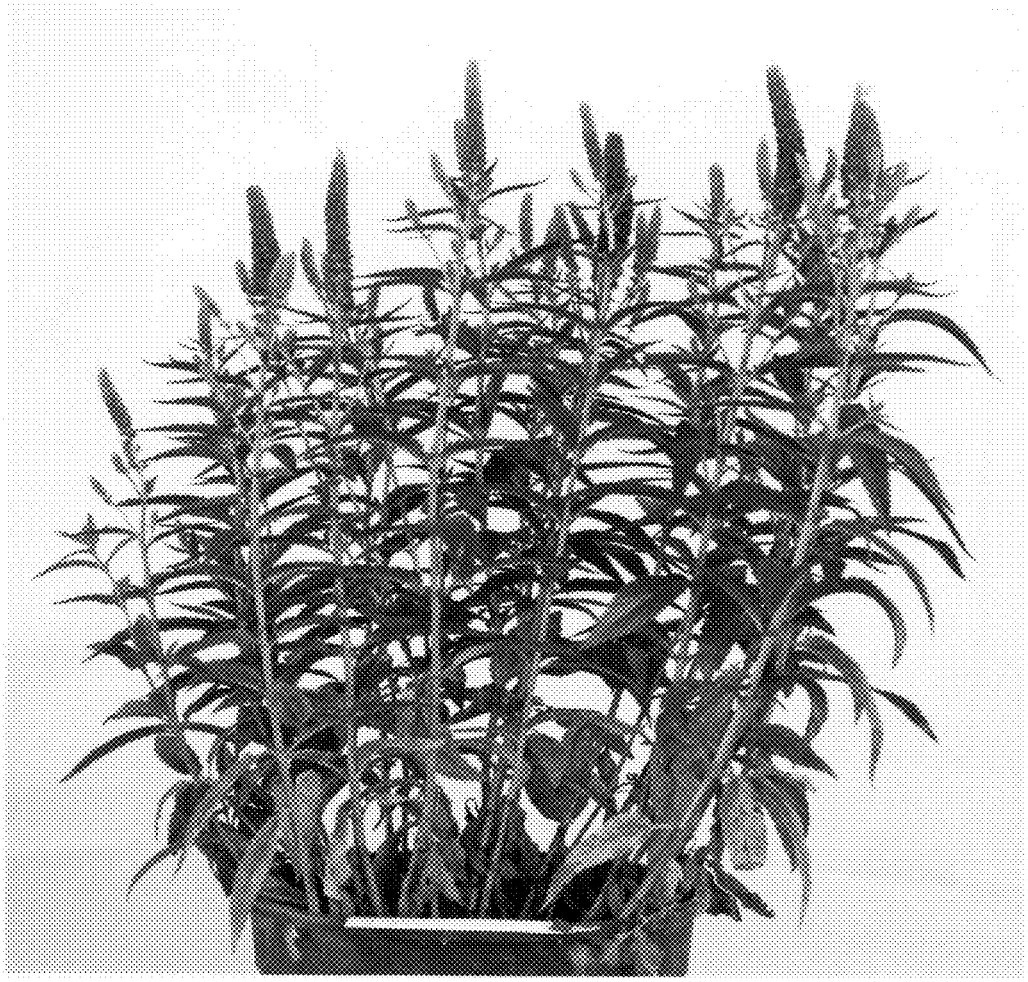

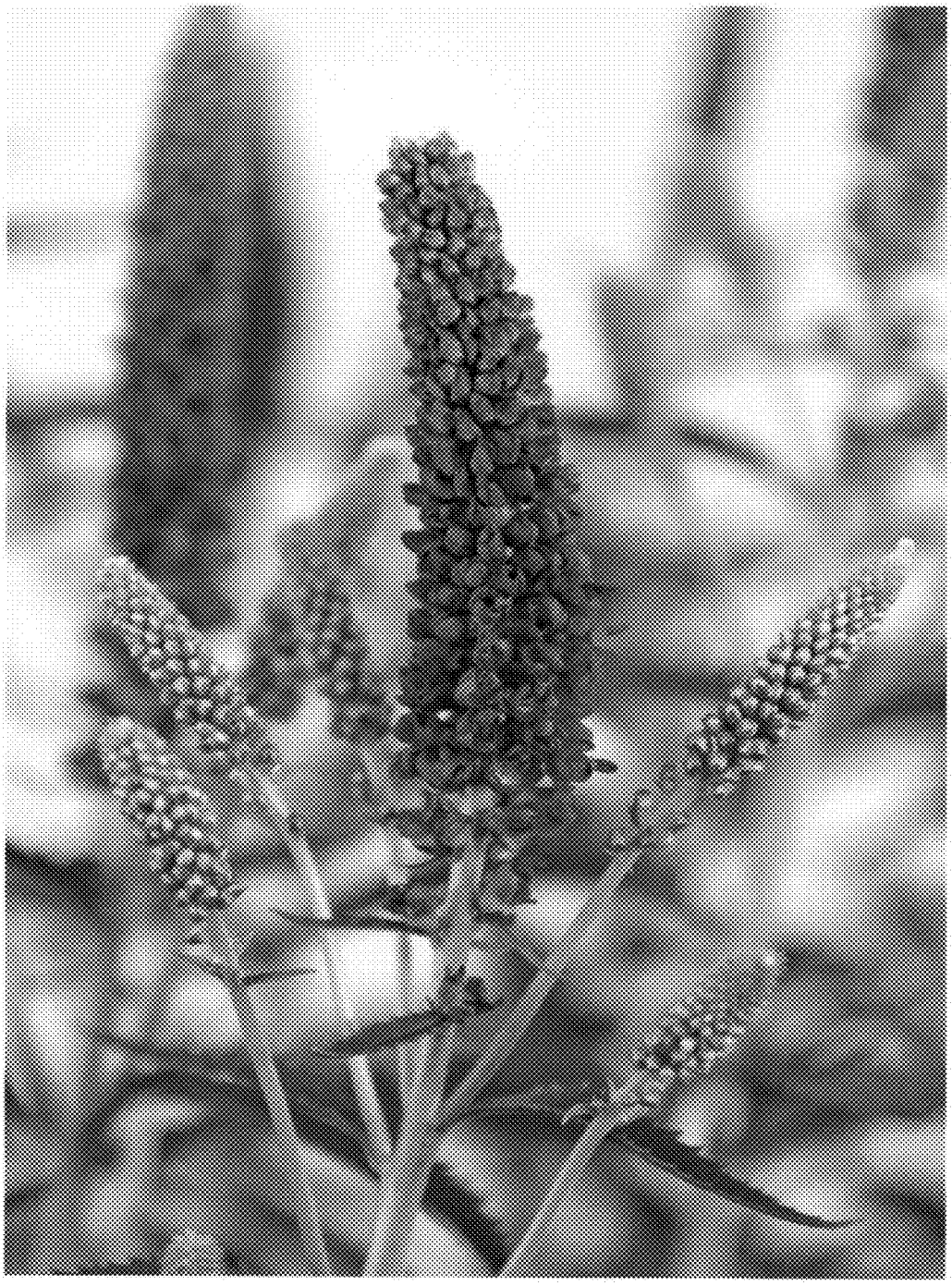

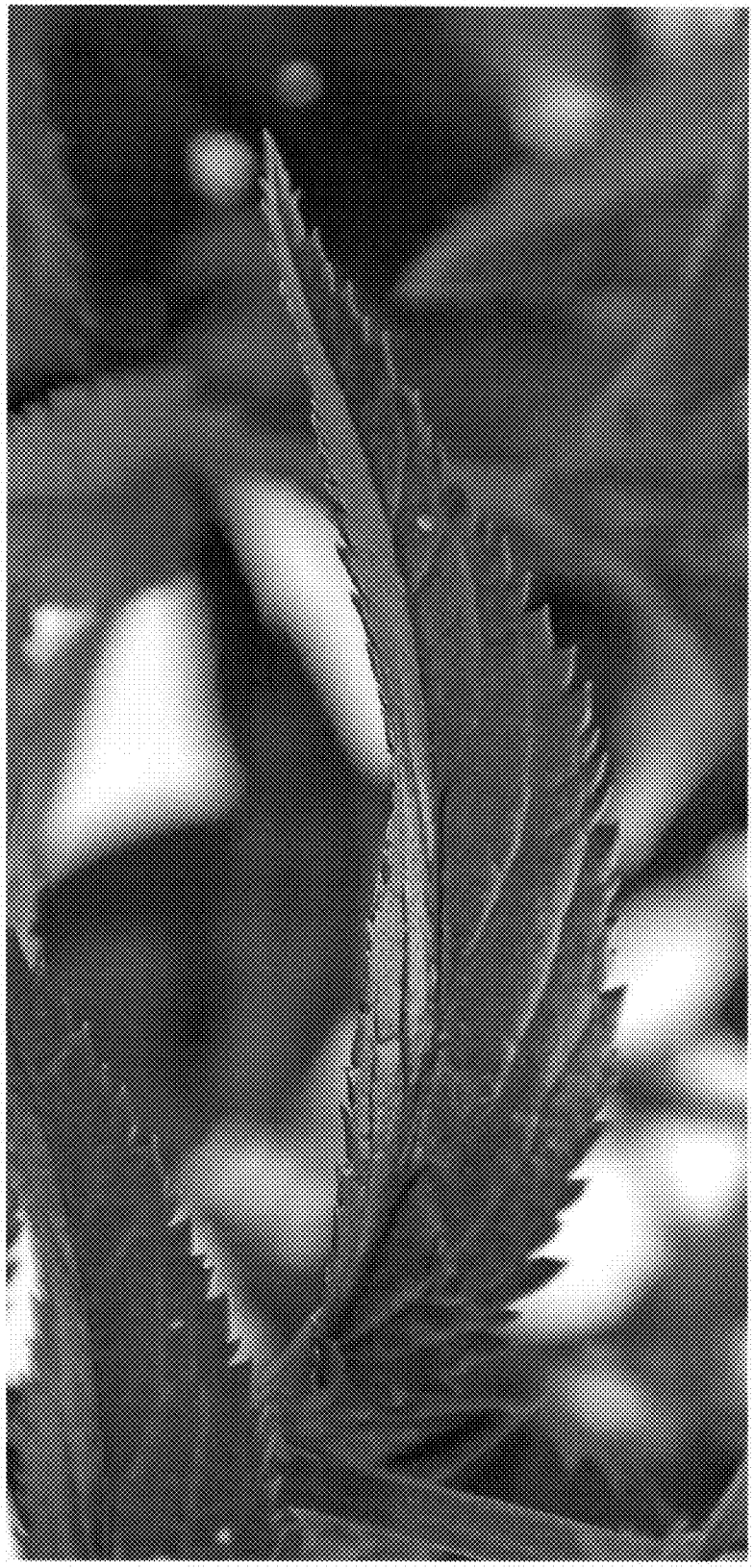

* * * * *